(12) United States Patent
Angel et al.

(10) Patent No.: US 8,808,323 B2
(45) Date of Patent: Aug. 19, 2014

(54) CONFIGURATION AND METHOD FOR FIXATION OF A FILTER TO A CATHETER

(75) Inventors: Luis F. Angel, San Antonio, TX (US); Jeffrey N. Steinmetz, Arvada, CO (US)

(73) Assignee: BiO2 Medical, Inc., San Antonio, TX (US)

( * ) Notice: Subject to any disclaimer, the term of this patent is extended or adjusted under 35 U.S.C. 154(b) by 314 days.

(21) Appl. No.: 13/333,811

(22) Filed: Dec. 21, 2011

(65) Prior Publication Data

US 2012/0158039 A1   Jun. 21, 2012

Related U.S. Application Data

(60) Provisional application No. 61/425,738, filed on Dec. 21, 2010.

(51) Int. Cl.
| | | |
|---|---|---|
| *A61M 29/00* | (2006.01) | |
| *A61B 17/24* | (2006.01) | |
| *A61F 2/01* | (2006.01) | |
| *B29C 65/02* | (2006.01) | |
| *B29C 65/10* | (2006.01) | |
| *B29C 65/00* | (2006.01) | |
| *A61M 25/06* | (2006.01) | |
| *B29L 31/14* | (2006.01) | |
| *A61M 25/00* | (2006.01) | |
| *B29C 65/68* | (2006.01) | |
| *A61B 17/221* | (2006.01) | |

(52) U.S. Cl.
CPC ............ *A61M 25/0009* (2013.01); *B29C 65/02* (2013.01); *B29C 65/10* (2013.01); *B29C 66/52272* (2013.01); *B29C 66/348* (2013.01); *A61F 2230/0006* (2013.01); *A61M 2025/0681* (2013.01); *A61F 2/01* (2013.01); *B29C 66/304* (2013.01); *A61F 2002/016* (2013.01); *B29L 2031/14* (2013.01); *B29L 2031/7572* (2013.01); *A61M 2025/0036* (2013.01); *B29C 65/68* (2013.01); *A61B 2017/2212* (2013.01); *A61F 2/013* (2013.01); *A61F 2230/008* (2013.01); *B29C 66/532* (2013.01); *A61F 2230/0093* (2013.01)
USPC .......................................... 606/200; 606/113

(58) Field of Classification Search
USPC .................................. 606/191, 194, 198, 200
See application file for complete search history.

(56) References Cited

U.S. PATENT DOCUMENTS

| | | | |
|---|---|---|---|
| 6,391,044 B1 | 5/2002 | Yadav et al. | 606/200 |
| 6,537,294 B1 | 3/2003 | Boyle et al. | 606/200 |

(Continued)

FOREIGN PATENT DOCUMENTS

| | | | | |
|---|---|---|---|---|
| WO | WO 01/49215 | 7/2001 | | A61F 2/06 |
| WO | WO 2009/029861 | 3/2009 | | A61M 5/00 |
| WO | WO 2011/085266 | 7/2011 | | A61M 5/00 |

OTHER PUBLICATIONS

Angel, L., et al., "In vitro placement and effectiveness of the angel™ vena cava filter catheter" *ISET Conference*, Miami, FL (Feb. 2010).

(Continued)

*Primary Examiner* — Tuan V Nguyen
(74) *Attorney, Agent, or Firm* — David G. Rosenbaum; J. Peter Paredes; Rosenbaum IP, P.C.

(57) ABSTRACT

An attachment configuration for a vascular filter assembly including a self-expanding filter member attached to a catheter body and constrained from expansion in a first configuration by a constraining sheath is presented. The attachment configuration includes an outer tube of material that is overlaid over an end of the filter member and bonded to the catheter body through cutouts disposed through the end of the filter member.

17 Claims, 7 Drawing Sheets

(56) References Cited

U.S. PATENT DOCUMENTS

| | | | |
|---|---|---|---|
| 6,936,058 B2* | 8/2005 | Forde et al. | 606/200 |
| 2003/0004540 A1 | 1/2003 | Linder et al. | 606/200 |
| 2004/0167565 A1 | 8/2004 | Beulke et al. | 606/200 |
| 2005/0010245 A1* | 1/2005 | Wasicek | 606/200 |
| 2006/0089663 A1 | 4/2006 | Gilson et al. | 606/200 |
| 2009/0062840 A1 | 3/2009 | Angel | 606/200 |
| 2010/0217304 A1 | 8/2010 | Angel et al. | 606/200 |
| 2011/0288578 A1 | 11/2011 | Angel | 606/198 |

OTHER PUBLICATIONS

Decousus, H., et al., "A clinical trial of vena caval filters in the prevention of pulmonary embolism in patients with proximal deep-vein thrombosis" *The New England Journal of Medicine* 338(7): 409-415 (1998).

Greenfield, L., et al., "A new intracaval filter permitting continued flow and resolution of emboli-surgery" *Surgery* 4: 599-606 (1973).

Lin, P., et al., "Vena caval filters in the treatment of acute DVT" *Endovascular Today* pp. 40-50 (Jan. 2005).

Mobin-Uddin, K., et al., "Experimental Prevention of Myocardial Infarction by Bronchial Collateral Circulation" *Journal of the American Medical Association* 208(2): 301-306 (1969).

International Preliminary Report on Patentability issued in corresponding foreign application, PCT/US2011/066637, pp. 1-6 (Jul. 4, 2013).

Extended Search Report, issued in corresponding foreign application, EP 11851729.1, pp. 1-5 (May 16, 2014).

* cited by examiner

CONFIGURATION AND METHOD FOR FIXATION OF A FILTER TO A CATHETER

CROSS-REFERENCE TO RELATED APPLICATIONS

The present application claims priority to the U.S. Provisional Application Ser. No. 61/425,738, filed Dec. 21, 2010, hereby incorporated by reference in its entirety.

FIELD OF THE INVENTION

The present invention pertains generally to the field of vascular filters for capturing embolic material in blood flow. More particularly, the present invention relates to a configuration and method for attachment of a vena cava filter near the distal end of a multi-lumen central access catheter.

BACKGROUND OF THE INVENTION

Venous thromboembolism (VTE), which includes deep venous thrombosis (DVT) and its sequela, pulmonary embolism (PE), is a significant clinical problem. It is the leading cause of preventable in-hospital mortality in the United States and in other developed countries. It is estimated that as many as 50% of patients in intensive care units are at risk of VTE and its comorbid conditions.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. (Decousus H, Leizorovicz A, Parent F, et al. *A clinical trial of vena caval filters in the prevention of pulmonary embolism in patients with proximal deep-vein thrombosis. N Engl J Med* 1998; 338:409-415). This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion.

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these include the Günther Tulip (Cook Inc.), Opt Ease (Cordis Corp.), and Recovery nitinol filters (Bard Peripheral Vascular, Tempe, Ariz.) (Lin P H, et al., *Vena caval filters in the treatment of acute DVT. Endovascular Today* 2005; January: 40-50). The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates. Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

In addition to providing a vascular filter for endoluminally trapping emboli while simultaneously preserving vascular flow, vascular filter assemblies ("VFA's") known in the art include additional features including, for example, a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Note that a jugular approach necessitates that the VFA be introduced retrograde relative to the vector of blood flow within the vena cava, i.e., the VFA is introduced through the jugular vein and directed inferiorly toward an infrarenal position. Additionally, since the blood flow opposes the distal end of the VFA and passes toward the proximal end, the vena cava filter must open inferiorly such that its largest diametric section in apposition to the vessel walls opens toward the distal end of the VFA rather than toward the proximal end of the VFA as with the femoral approach.

The VFA may include fluid infusion ports positioned in the sidewall of the central access catheter to which the vascular filter is attached. Such fluid infusion ports may have a directional flow orientation such that any or all regions of the space delimited by the vena cava filter may be exposed to fluid flow therefrom.

The VFA may include proximal and distal ports disposed in the central access catheter and positioned entirely or partially distant from an open area bounded by the filter permit measuring pressure and/or flow velocity across the filter as a determinant of extent of capture of embolic material in the filter or for measuring flow rate at the position of the filter member as a positional indicator within the body. Such pressure and/or flow sensing may be accomplished by a hydrostatic fluid column in communication with each of the proximal and distal ports and a pressure transducer operably associated with a proximal end of the central access catheter.

The proximal and distal ports, and lumens associated therewith, may also provide means for introducing fluids, such as an anticoagulant, thrombolytic or other bioactive agents, contrast medium, blood transfusions, intravenous fluids or other medications. Alternatively, the proximal and distal ports may be used for withdrawal or evacuation of fluids or other material through the catheter. The multiple infusion ports also provide a means for introducing a flushing medium, such as saline, under elevated pressure to produce mechanical thrombolysis or induce thrombolysis by the infusion of thrombolytic agents directly to thrombus within the filter.

A need exists for a configuration and method for attachment of the filter to a catheter that is mechanically reliable and simple to manufacture.

SUMMARY OF THE INVENTION

An attachment configuration disposed at a proximal end of a filter member comprises a catheter body coaxially disposed through the proximal end of the filter member; a plurality of cutouts disposed coaxially around the proximal end of the filter member; and a thin tube coaxially disposed around the plurality of cutouts, wherein the thin tube engages the at least a portion of the catheter body and the thin tube fixedly attaches the proximal end of the filter member through the plurality of cutouts.

A method for attaching a proximal end of a filter member, comprises disposing a thin tube over a catheter body and over at least a portion of the proximal end of the filter member, wherein the proximal end includes a plurality of cutouts; disposing a heat shrink tube coaxially over the thin tube; and fusing the thin tube to the catheter body through the plurality of cutouts to attached the proximal end of the filter member to the catheter body.

The foregoing and other features and advantages of the invention are apparent from the following detailed description of exemplary embodiments, read in conjunction with the accompanying drawings; wherein like structural or functional elements may be designated by like reference numerals.

BRIEF DESCRIPTION OF THE DRAWINGS

The foregoing and other features and advantages of the invention are apparent from the following detailed description of exemplary embodiments, read in conjunction with the accompanying drawings; wherein like structural or functional elements may be designated by like reference numerals.

DETAILED DESCRIPTION OF THE PREFERRED EMBODIMENTS

In the accompanying Figures like structural or functional elements are designated by like reference numerals, e.g., 16, 116, 216, 316, 416 represent similar structural or functional elements across different embodiments disclosed herein.

As used in this application, unless otherwise specifically stated, the terms "proximal" and "distal" are intended to refer to positions relative to a longitudinal axis of the VFA. Those skilled in the art will understand that the VFA has a distal end which is first inserted into a patient and a proximal end which opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head.

The embodiments disclosed herein may be configured for either a femoral approach or a jugular approach to the inferior vena cava. Vena cava filters are typically deployed infrarenally, but may also be deployed suprarenally. It will be understood that within the inferior vena cava blood flow is superior, i.e., toward a patients head. Thus, in all embodiments, the vena cava filter will be positioned so that it opens inferiorly, i.e., away from the patient's head and toward the direction of the blood flow. It will be appreciated, therefore, that in the embodiments disclosed herein, the vena cava filter will have a different axial orientation on the central access catheter depending upon whether the device is intended for use in a femoral approach or a jugular approach.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Figure 1:
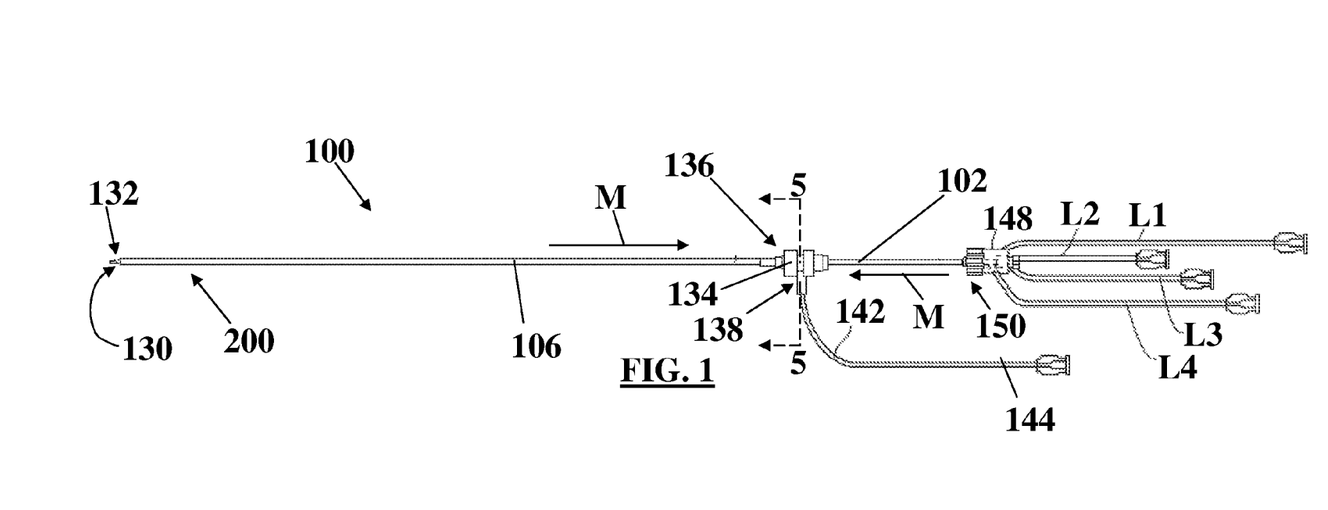
FIG. 1 is a side elevational view of an exemplary vascular filter assembly in a first configuration.
Figure 2:
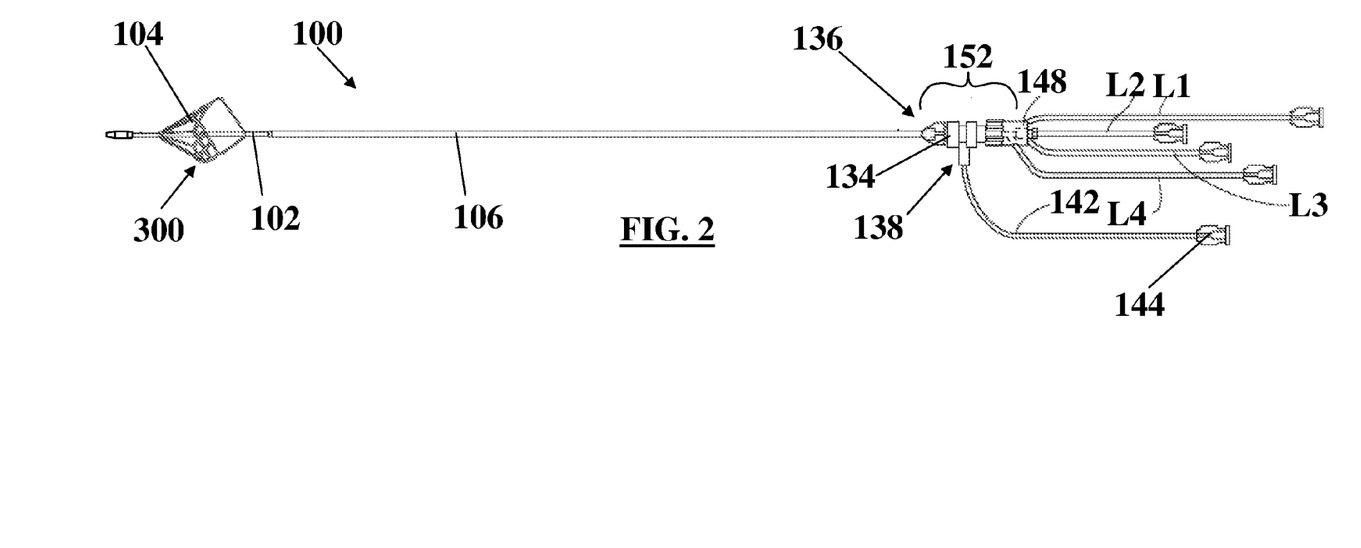
FIG. 2 is a side elevational view of the exemplary vascular filter assembly of FIG. 1 in a second configuration.

Referring to FIGS. 1 and 2, an exemplary vascular filter assembly ("VFA") 100 is illustrated in a first configuration 200 and a second configuration 300, respectively. The exemplary VFA 100 includes a catheter body 102 having a self-expanding filter member 104 coupled thereto. A sheath 106 is disposed over the filter member 104 and the catheter body 102 such that the filter member 104 is at least partially constrained from expansion in the first configuration 200. The filter member 104 is constrained from expansion within an interior space 108 (See FIGS. 5 and 6) defined between the sheath 106 and the catheter body 102.

The filter member 104 may be slidably or fixedly attached to the catheter body 102 or may be removably coupled to the catheter body 102 for deployment as either a permanent filter or as a temporary and retrievable vena cava filter. Removable coupling of the filter member 104 to the catheter body 102 may be accomplished with a variety of release and retrieval mechanisms operably associated with the catheter body 102. Non-limiting examples of such release and retrieval mechanisms are disclosed, for example, in Angel U.S. Patent Application Publication No. 2009/0062840 and Angel et al. U.S. Patent Application Publication No. 2010/0217304, incorporated by reference in their entirety herein.

Figure 5:
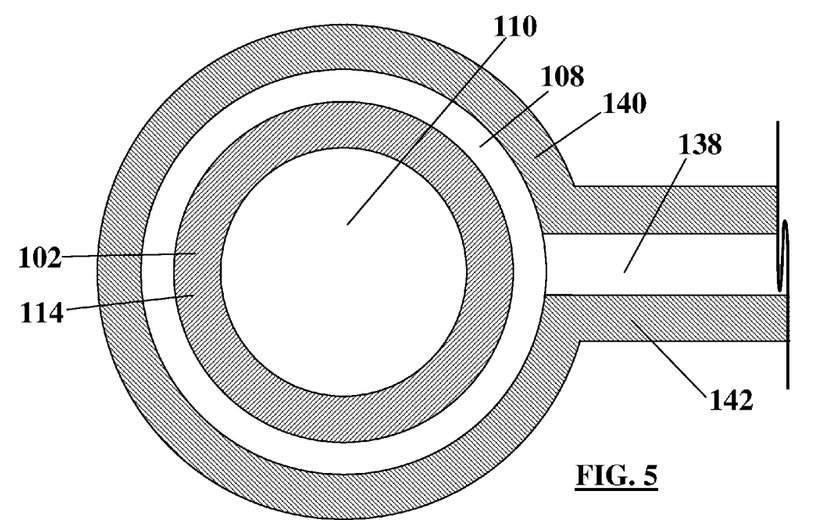
FIG. 5 is a cross-sectional view of an exemplary vascular filter assembly taken generally along line 5-5 of FIG. 1.

Referring to FIG. 5, in one embodiment, the catheter body 102 comprises a single lumen 110. The single lumen 110 is in fluid communication with the interior space 108 via at least one port 112 disposed through the sidewall 114 of the catheter body 102.

Figure 6:
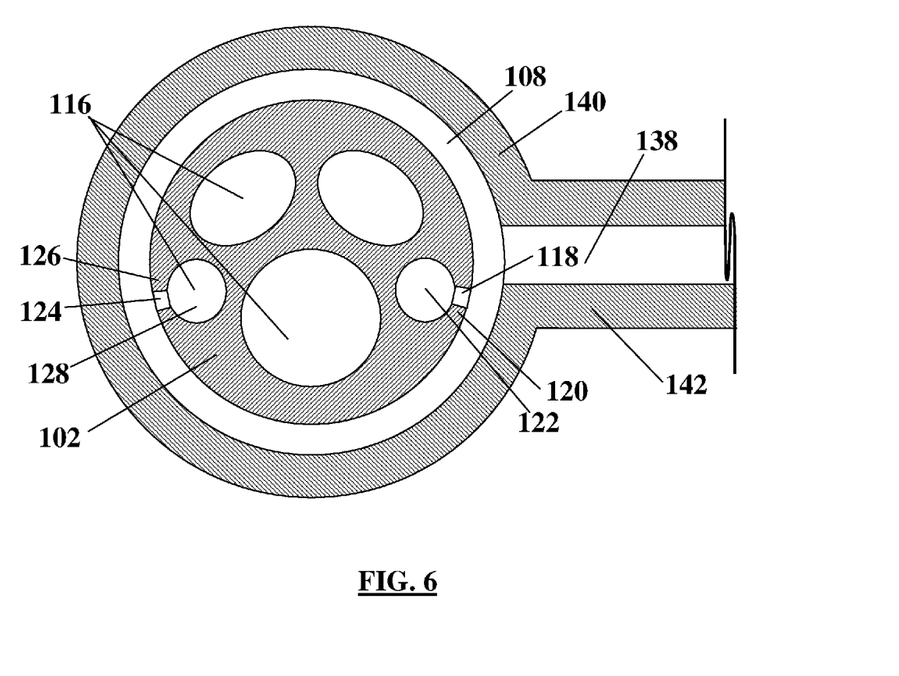
FIG. 6 is a cross-sectional view of another exemplary vascular filter assembly taken generally along line 5-5 of FIG. 1.

Referring to FIG. 6, in other embodiments, the catheter body 102 comprises multiple lumens 116. In one embodiment, the catheter body 102 includes at least one first port 118 disposed through a sidewall 120 thereof and providing fluid communication between the interior space 108 and a first lumen 122. The catheter body 102 may further include at least one second port 124 disposed through a sidewall 126 thereof and providing fluid communication between the interior space 108 and a second lumen 128. Bioactive agents, flushing fluids, pressurized mechanical thrombolytic fluids, or other fluids may be infused through the single lumen 110 or the first and second lumens 122, 128 and out of the at least one port 112, the at least one first port 118, and the at least one second port 124 to pass into the interior space 108 and ultimately into a patient's venous system for either local or systemic effect.

Again referring to FIGS. 1 and 2, the sheath 106 may be concentrically disposed over the catheter body 102 such that relative longitudinal movement of the catheter body 102 and the sheath 106 (as indicated by arrows labeled M in FIG. 1) either exposes the filter member 104 in the second configuration 300 or captures the filter member 104 within the sheath 106 in the first configuration 200. The sheath 106 may terminate in an annular opening 130 (corresponding to the interior space 108) at a distal end 132 thereof. A distal hub 134 may be coupled to a proximal end 136 of the sheath 106.

Referring to FIGS. 1, 2, 5 and 6, an infusion port 138 may be provided disposed through a sidewall 140 of the sheath 106. The infusion port 138 is adapted to receive a tube 142 that may include a luer or other type of fitting 144 at a proximal end thereof. The infusion port 138 provides fluid communication between an exterior of the distal hub 134 and the interior space 108, as illustrated in FIGS. 5 and 6.

A proximal hub 148 may be coupled to a proximal end 150 of the catheter body 102. The proximal hub 148 and the distal hub 134 may be removably engageable with each other. A plurality of fluid lines, for example, fluid lines L1, L2, L3, L4, may communicate with the proximal hub 148, as illustrated in FIGS. 1 and 2. Each of the fluid lines L1, L2, L3, and L4 may be in fluid communication with at least one of the single lumen 110, the first and second lumens 122, 128, or other lumens within the catheter body 102. When the VFA is in the second configuration 300, the proximal and distal hubs 148, 134 may be removably engaged to form a hub assembly 152 that inhibits relative motion of the catheter body 102 and the sheath 106. Vascular filter assemblies and features thereof such as structure, orientation, and materials comprising the filter member 104, the sheath 106 and/or the catheter body 102 including single or multiple lumens that may be instructional or useful in the current application may be found in the disclosures of, for example, Angel U.S. Patent Application Publication No. 2009/0062840 and Angel et al. U.S. Patent Application Publication No. 2010/0217304, incorporated by reference in their entirety.

Figure 3:
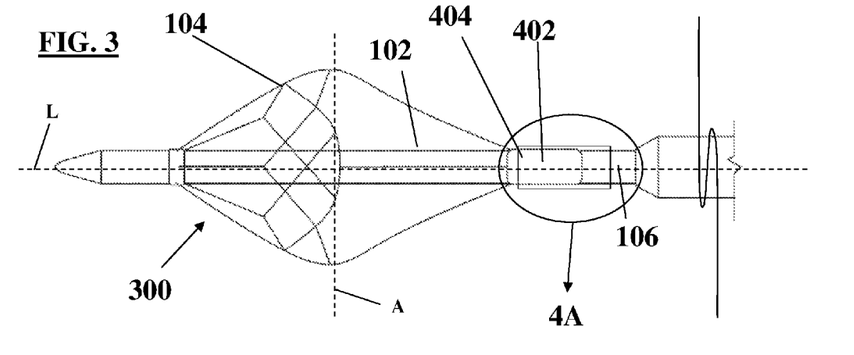
FIG. 3 is a close-up view of a distal end of the exemplary vascular filter assembly of FIG. 1 in a second configuration.
Figure 4A:
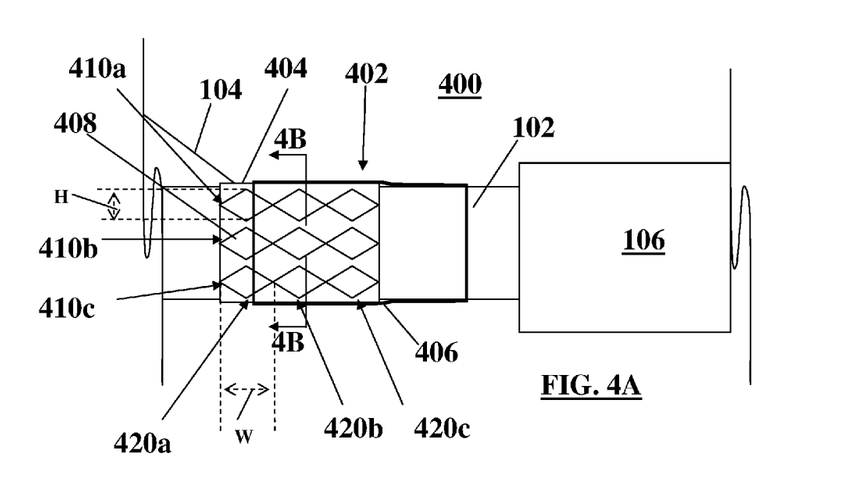
FIG. 4A is a close-up view of area 4A of FIG. 3 for an attachment configuration for the exemplary vascular filter assembly.
Figure 4B:
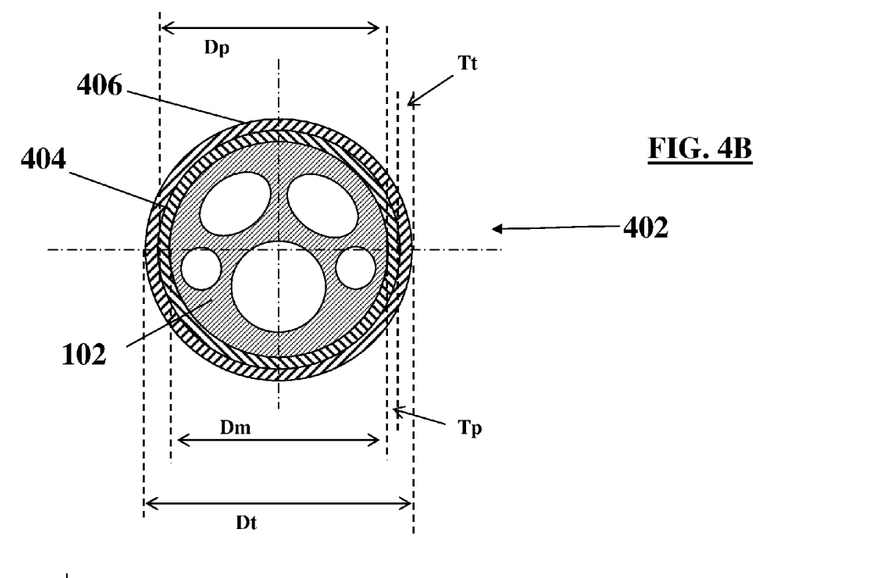
FIG. 4B is a cross-sectional view of the attachment configuration of FIG. 4A taken generally along the line 4B-4B of FIG. 4A.

Referring to FIG. 3-4B, in one embodiment of a VFA 400, an embodiment of attachment configuration 402 disposed at a proximal end 404 of the filter member 104 attaches the filter member 104 to the catheter body 102. The general longitudinal axis L and axial axis A is shown in FIG. 3. The catheter body 102 is coaxially disposed through the proximal end 404 of the filter member 104. Preferably, the catheter body 102 is coaxially disposed through the interior of the proximal end 404, as shown in FIG. 4B. However, alternatively, the catheter body 102 may be coaxially disposed on the exterior of the proximal end 404. In one embodiment, the proximal end 404 of the filter member 104 includes a plurality of cutouts 408 disposed coaxially around the proximal end 404 of the filter member 104. A thin tube 406 is disposed coaxially around the plurality of cutouts 408 as to engage at least a portion of the catheter body 102 through the plurality of cutouts 408.

In one embodiment, the material of a thin tube 406 (See FIGS. 4A and 4B) and the material of the catheter body 102 are the same as to be fused together through the plurality of cutouts 408. However, in other embodiments, the proximal end 404 of the filter member 104 may not include cutouts 408 or may include cutouts 408 having a diamond shape as generally shown in FIG. 4A or other patterns or shapes, including, but not limited, triangular, pyramidal, square, rectangular, polygonal, pentagonal, hexagonal, octagonal, circular, elliptical, open-ended circular shape, semi-circular shapes, coiled shapes, zig-zag shapes, sinusoidal shapes, spaced-lines, and the like. Alternatively, the cutouts 408 may include a combination of different shapes and patterns, as further explained below.

The plurality of cutouts 408 include a width W extending generally along the longitudinal axis of the proximal end 404 and a height H extending generally along the axial axis of the proximal end 404, as shown in FIG. 4A. The width W and height H of the plurality of cutouts 408 may be adjusted as to maximize the engagement of the thin tube 406 through the cutouts 408 and with the catheter body 102. In one embodiment, the width W of the cutouts 408 is greater than the height H of the cutouts as to maximize the longitudinal engagement of the proximal end 404 with the catheter body 102. Generally speaking, the filter member 104 experiences longitudinal forces once the filter member 104 is in the second configuration 300, due to direction of blood flow and captured embolisms. As shown in FIG. 4B, the proximal end 404 includes a thickness Tp, whereby the plurality of cutouts 408 traverse the entire thickness Tp of the proximal end. Also, the thin tube 406 includes a thickness Tt. In one embodiment, the thickness Tt of the thin tube 406 is less than the thickness Tp of the proximal end 404 such that the thin tube 406 may properly traverse the thickness Tp of the proximal end 404 to engage the catheter body 102. The thin tube 406 includes a diameter Dt, the proximal end 404 includes a diameter Dp, and the multilumen catheter body 102 includes a diameter Dm. Preferably, the diameter Dt of the thin tube 406 is greater than the diameter Dp of the proximal end 404, and the diameter Dp of the proximal end 404 is greater than the diameter Dm of the catheter body 102. Alternatively, the diameters Dt, Dp, and Dm may be of the similar sizes, such that diameter Dp is radially expandable to constrict onto the catheter body 102, and the diameter Dt radially expands to constrict onto the proximal end 404.

In one embodiment, the plurality of cutouts 408 are longitudinally disposed throughout the proximal end 404 of the filter, that is the cutouts 408 extend generally parallel along the longitudinal axis. The longitudinal extension of the cutouts 408 provides a series of longitudinal rows of cutouts 410, i.e. a first longitudinal row of cutouts 410a, a second longitudinal row of cutouts 410b, and a third longitudinal row of cutouts 410c, as shown in FIG. 4A. Generally, at least two rows of the longitudinal cutouts are provided. The longitudinal rows of cutouts 410a, 410b, and 410c may generally include at least three cutouts 408 along the longitudinal axis, alternatively, the longitudinal row of cutouts may include at least two cutouts 408, at least four cutouts, at least five cutouts, at least six cutouts, or at least between two and 20 cutouts along the longitudinal axis. The number of cutouts 408 along the longitudinal axis for each longitudinal row 410a, 410b, and 410c may be the same or different, or alternatively, the number of cutouts 408 for each longitudinal row of cutouts 410a, 410b, and 410c may be selected based upon the degree of attachment for the proximal end 404 to the catheter body 102. While three longitudinal rows of cutouts 410a, 410b, and 410c are shown in FIG. 4A, the attachment configuration 402 may include at least two rows of cutouts, at least four rows of cutouts, at least five rows of cutouts, at least six rows of cutouts, or at least between two and 20 rows of cutouts along the longitudinal axis. In one embodiment, each cutout 408 in the longitudinal row of cutouts is adjacent or touching adjacent cutouts 408 along the Width W of the cutouts, such that adjacent cutouts 408 are touching in an end-to-end fashion along the Width W. Alternatively, adjacent cutouts 408 in each longitudinal row of cutouts 410 may include a space between adjacent ends of the cutouts 408 along the Width of the cutouts 408, as further explained below.

Also, the plurality of cutouts 408 may be disposed in a series of axial column of cutouts 420, i.e. a first axial column of cutouts 420a, a second axial column of cutouts 420b, and a second axial column of cutouts 420c, as shown in FIG. 4A. The thin tube 406 may be coaxially disposed over the second axial column of cutouts 420b and the third axial column of cutouts 420c. Alternatively, the thin tube 406 may be coaxially disposed to be partially overlapping the first axial column of cutouts 420a, or the thin tube 406 may not be coaxially disposed over the first axial column of cutouts 420a. Alternatively, the thin tube 406 may be coaxially disposed over first and second axial columns of cutouts 420a, 420b. The axial column of cutouts 420a, 420b, and 420c may generally include at least three cutouts 408 along the axial axis, alternatively, the axial column of cutouts 420 may include at least two cutouts 408 along the axial axis, at least four cutouts, at least five cutouts, at least six cutouts, or at least between two and twenty cutouts along the axial axis. The number of cutouts 408 along the axial axis for each axial column of cutouts 420a, 420b, and 420c may be the same or different, or alternatively, the number of cutouts 408 for each column of cutouts 420a, 420b, and 420c may be selected based upon the degree of attachment for the proximal end 404 to the catheter body 102. While three axial column of cutouts 420a, 420b, and 420c are shown in FIG. 4A, the attachment configuration 402 may include at least two axial columns of cutouts, alternatively, at least four axial columns, at least five axial columns, at least six axial columns, or at least between two and twenty axial columns along the axial axis. In one embodiment, each cutout 408 in the axial column of cutouts is adjacent or touching adjacent axial cutouts 408, such that adjacent cutouts 408 are touching in an end-to-end fashion along the height H of the cutouts 408. Alternatively, adjacent cutouts 408 in each axial column of cutouts 410 may include a space between adjacent ends of the cutouts 408 along the height H of the cutouts 408, as further explained below.

Figure 4C:
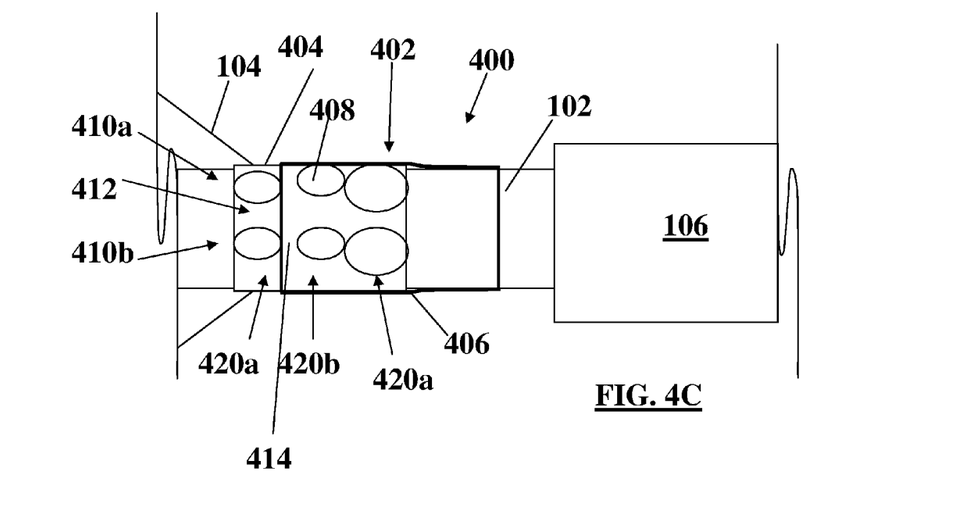
FIG. 4C is an alternative attachment configuration for the vascular filter assembly.

FIG. 4C shows an alternative configuration for the cutouts in the attachment configuration 402, where the cutouts 408 include a circular shape. In this embodiment, the first longitudinal row of cutouts 410a includes a space or gap 412 between the second longitudinal row of cutouts 410b. Also, the first axial column of cutouts 420a includes a space or gap 414 between the second axial column of cutouts 420b. Additionally, the thin tube 406 is coaxially disposed only over the second axial column and the third axial column of cutouts 420b, 420c. This coaxial disposition of the thin tube 406 attaches the proximal end 404 of the filter member 104 through the second axial column and the third axial column of cutouts 420b, 420c to the catheter body 102 while permitting the first axial column of cutouts 420a. And the third axial column of cutouts 420c includes a greater Width W and Height H compared to the second and first axial column of cutouts 420a, 420b.

Figure 4D:
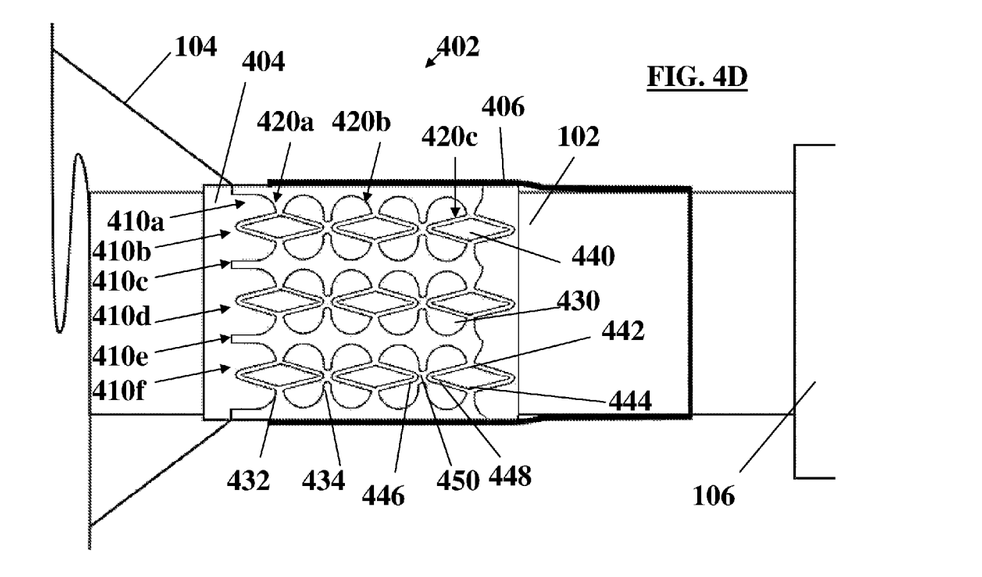
FIG. 4D shows an alternative configuration for the cutouts in the attachment configuration.

FIG. 4D shows an alternative configuration for the cutouts in the attachment configuration 402 including alternating cutouts of diamond shapes 440 and semi-circular shapes 430. The first, third, and fifth longitudinal row of cutouts 410a, 410c, 410e is a repeating pattern of semi-circular shape cutouts 430, whereby the semicircular shape cutouts 430 include a first leg 432 and a second 434 encircling the semi-circular cutout 430. The second, fourth, and sixth longitudinal rows of cutouts 410b, 410d, and 410f include a repeating pattern of diamond shaped cutouts 440, whereby the diamond shaped cutouts 440 include a strut-like enclosure with a top half 442 and a bottom half 444 enclosing the diamond shaped cutouts 440. The top half 442 and the bottom half 444 project generally along the axial axis of the proximal end 404. The diamond shaped cutouts 440 includes a first end 446 and a second end 448 projecting generally along the longitudinal axis of the proximal end 404. The top half 442 and the bottom half 444 of the diamond-shaped cutouts 440 are fixedly attached to the first legs 432 of the semi-circular cutouts 430. The first end 446 and the second end 448 generally cover at least a portion of the semi-circular cutouts 430, whereby the first end 446 and the second end 448 of adjacent diamond-shaped cutouts 440 include a space or gap 450 therebetween. In one embodiment, the gap 450 between the first axial column of cutouts 420a and the second axial column of cutout 420b is where the distal end of the thin tube 460 is positioned for attaching the proximal end 404 to the catheter body 102. Such an alternating pattern for the attachment configuration 402 may be radially expandable as to coaxially fit over the catheter body 102.

Figure 4E:
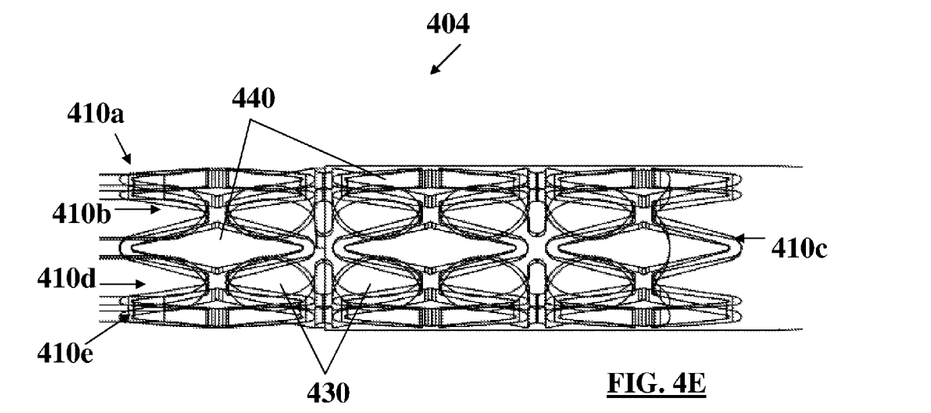
FIG. 4E shows an exploded view of the proximal end 404 including the alternating pattern from FIG. 4D.
Figure 4F:
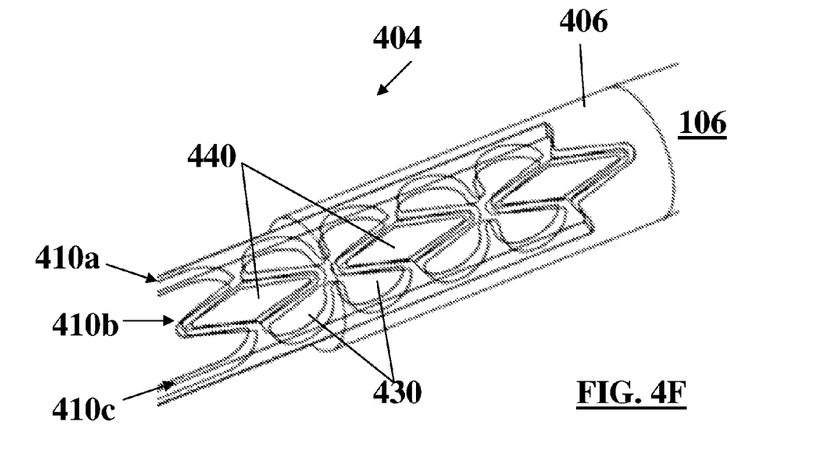
FIG. 4F shows a perspective view of the proximal end 404 including the alternating pattern of cutouts from FIG. 4D.

FIG. 4E shows an exploded view of the proximal end 404 including the alternating pattern from FIG. 4D. Here, the first longitudinal row of cutouts 410a includes the diamond-shaped cutouts 440, which extending generally along top of the proximal end 404. The second longitudinal row of cutouts 410b includes the semicircular shape cutouts 430, the third longitudinal row of cutouts 410c includes the diamond-shaped cutouts 440, the fourth longitudinal row of cutouts 410d include the semicircular shaped cutouts 430, the fifth longitudinal row of cutouts 410e includes the diamond shaped cutouts 440. FIG. 4F shows a perspective view of the proximal end 404 including the alternating pattern of cutouts from FIG. 4D. Here, the first longitudinal row of cutouts 410a includes the semicircular shape cutouts 430, which extending generally along top of the proximal end 404. The second longitudinal row of cutouts 410b includes the diamond-shaped cutouts 440, the third longitudinal row of cutouts 410c includes the semicircular shaped cutouts 430.

Figure 4G:
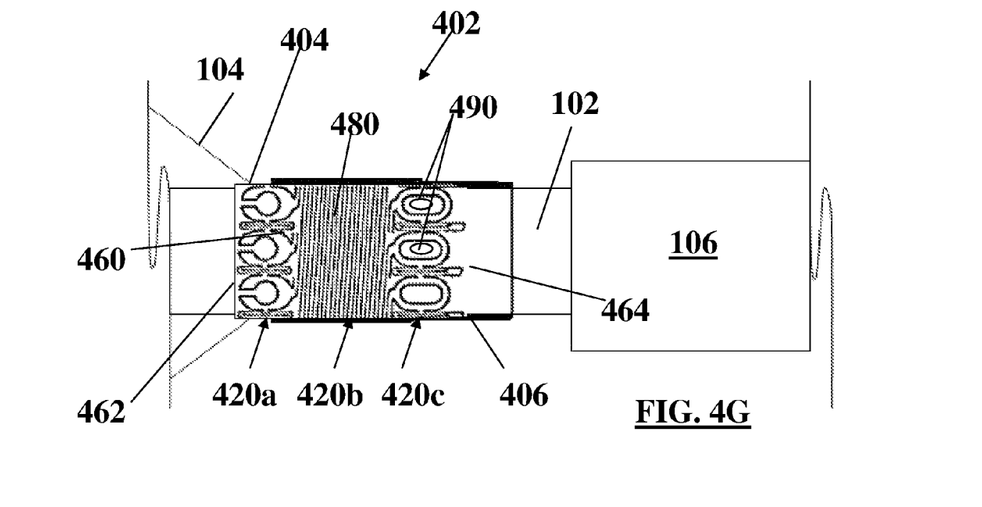
FIG. 4G shows an alternative configuration for the cutouts in the attachment configuration 402.

FIG. 4G shows an alternative configuration for the cutouts in the attachment configuration 402 including alternating cutouts of an open-ended circular shapes 460 on the first end 462 of the proximal end 404, an elliptical shaped cutouts 470 on the second end 464, and a coiled shape cutout 480 intermediate the open-ended circular shape cutouts 460 and the elliptical shaped cutouts 470. In this attachment configuration 402, the first axial column of cutouts 420a includes the open-ended circular shaped cutouts 460, the second axial column of cutouts 420b includes the coiled shaped cutouts 480, and the third axial column of cutouts 420c includes the elliptical shaped cutouts. The coiled shaped cutouts 480 provided flexibility while also permitting the thin tube 406 to engage and attached to the catheter body 102 between the coils. The elliptical shaped cutouts 470 may engage a detent or projection 490 on the catheter body 102 as to prevent longitudinal movement of the proximal end 404 upon attachment of the thin tube 406. The detent or projection 490 fitted to the elliptical shaped cutouts 470 may provide a point of connection for a user operating the catheter and the filer member 104.

Figure 4H:
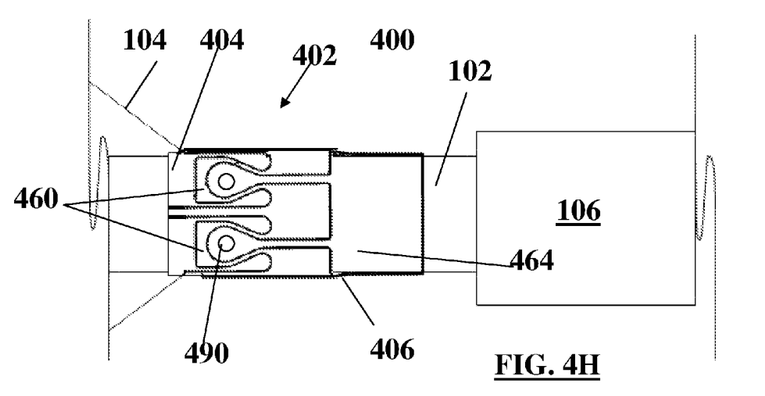
FIG. 4H shows an alternative configuration for the cutouts in the attachment configuration.

FIG. 4H shows an alternative configuration for the cutouts in the attachment configuration 402 including an open ended shape cutout 460 including an opening 468 facing the second end 464 of the proximal end 404. The opening 468 may allow for radial expansion, while the open-ended shape cutout 460 may engage a projection or detent 490 extending from the catheter body 102 as to prevent longitudinal movement of the proximal end 404 upon being attached to the catheter body 102 by the thin tube 406.

Referring now to all embodiments, the attachment configuration 402 is created by a thermal bonding process including first inserting polymer coated metal wires into a single lumen of the single lumen catheter body 102 or into multiple lumens of the multilumen catheter body 102. In one embodiment, the polymer coating for the metal wires is polytetrafluorethylene (PTFE), although other polymers may be used as indicated below. The polymer coated metal wires placed into the lumen or lumens inhibit closure or filling of the lumen or lumens in the rest of the process and therefore function to maintain patency of the lumen or lumens.

Next, a thin tube 406 is coaxially disposed over the catheter body 102 and coaxially over at least a portion of the proximal end 404 of the filter member 104 as illustrated in FIG. 4A. In one embodiment, the tube 406 comprises a polyether block amide, for example, sold under the trademark name PEBAX®, available from the Arkema Company, Colombes Cedex, France. In other embodiments, the thin tube 406 may be made from other materials. In one embodiment, the thin tube 406 is made from the same material as the catheter body 102, for example, a polyether block amide sold under the trademark name PEBAX®. In this embodiment, the cutouts 408 in the end 404 of the filter member 104 allow the same material of the thin tube 406 and the catheter body 102 to flow together through the cutouts 408 when melted.

A polyethylene terephthalate (PET) heat shrink tube (not shown) is disposed over the thin tube 406. Alternative polymer heat shrink tubes may be used, such as fluorinated ethylene propylene (FEP) provided that the polymer heat shrink tube is not the same material as the thin tube 406 or the catheter body 102. In one embodiment, the thin tube is fused to the catheter body 102 through the plurality of cutouts 408 using, for example, hot air as provided from a hot air nozzle. In other embodiments, the fusing may be supplied in alternative ways such as a thermal bonder, thermoplastics, and the like. For portions of the proximal end that are not to be bonded by the thin tube 406, a heat shield may be used to protect such areas of the proximal end 404 to prevent fusing. Heating the attachment configuration 402 causes the material of the thin tube 406 and the material of the catheter body 102 to melt together. In one embodiment, the melting together of the thin tube 406 and the catheter body 102 causes contact and bonding therebetween through the cutouts 408. Effectiveness of such contact and bonding may be increased in embodiments where the thin tube 406 and the catheter body 102 are made of the same material, which upon melting can flow together through the cutouts 408 into a seamless monolithic structure that encapsulates the end 404 of the filter 104 as illustrated in FIGS. 4A-4G. Following the step of applying heat to melt the thin tube 406, the PET heat shrink tube may be removed thus completing the process of making the attachment configuration 402.

The catheter body 102 in the region of the attachment configuration 402 may be the single lumen catheter body 102 as illustrated in FIG. 5, or the multilumen catheter body as illustrated in FIG. 6, or as configured including other lumens different from those illustrated in FIG. 6. It should also be noted that any or all of the lumens in the multilumen catheter body of FIGS. 4B and/or FIG. 6 may extend only partially through the catheter body 102 or entirely through the catheter body 102.

Alternative polymeric materials may be included for the thin tube 406, such as, for example, polytetrafluoroethylene (PTFE), ethylene tetrafluoroethylene (ETFE), fluorinated ethylene propylene (FEP), polyoxymethylene (POM, for example, as sold under the trademark DELRIN® available from DuPont), polybutylene terephthalate (PBT), polyether block ester, polyurethane, polypropylene (PP), polyvinylchloride (PVC), polyether-ester (for example, a polyether-ester elastomer as sold under the trademark ARNITEL® available from DSM Engineering Plastics), polyester (for example, a polyester elastomer as sold under the trademark HYTREL® available from DuPont), polyamide (for example, as sold under the trademark DURETHAN® available from Bayer or as sold under the trademark CRISTAMID® available from Elf Atochem), elastomeric polyamides, block polyamide/ethers, polyether block amide (PEBA, for example, as sold under the trade name PEBAX® available from Arkema, Inc.), silicones, polyethylene (PE), Marlex high-density polyethylene, Marlex low-density polyethylene, linear low density polyethylene, polyethylene terephthalate (PET), polyetheretherketone (PEEK), polyimide (PI), polyetherimide (PEI), polyphenylene sulfide (PPS), polyphenylene oxide (PPO), polysulfone, nylon, nylon-12 (as sold under the trademark GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. Alternatively, the thin tube 406 may be fabricated from shape memory materials, including shape memory metals and shape memory polymers ("SMM").

The filter member 104 and the proximal end 404 may be fabricated of biocompatible materials, such as shape memory metal alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel. Alternatively, biocompatible polymers may be used to fabricate the filter member 104 and the proximal end 404. The plurality of cutouts may be formed by laser cutting, wet or dry etching, and similar methods for creating cutouts in metal materials.

In addition, a placement sensor may be coupled to the proximal end 404 to determine the degree of attachment for the configuration 402. Such a placement sensor may provide indications on whether the proximal end 404 is moving along the longitudinal axis of the catheter body 102 after affixation. If movement of the proximal end 404 is detected by the user, the user may then retract the catheter body as to prevent the filter member 104 from being retracted to the first configuration 200 or the filter member being dislodged in the patient.

While the embodiments disclosed herein are not limited to specific dimensional sizes of the catheter body 102, the sheath 106, or any lumen diameter or port dimension, an exemplary outer diameter size of the sheath 106 is between about 6 Fr (2.0 mm) and about 9 Fr (3.0 mm). An exemplary outer diameter size of the catheter body 102 is between about 4 Fr (1.3 mm) and 7 Fr (2.4 mm).

An attachment configuration for a vascular filter assembly ("VFA") including a self-expanding filter member attached to a catheter body and constrained from expansion in a first configuration by a low profile constraining sheath is presented. The attachment configuration is simple to produce and provides an effective and reliable bond between the filter member and the catheter body.

Vena cava filter placement frequently occurs concomitantly with central access line placement or in critically ill patients that already have a central access line in place. Heretofore, however, there have been no devices which combine the function of a central access catheter and a removable vena cava filter.

The embodiments disclosed herein benefit from an improved method for coupling a multi-lumen catheter to a vena cava filter such that the multi-lumen catheter is useful both as a central venous access catheter for administration of intravenous fluids, bioactive agents, contrast agents, flushing agents, pressurized fluids for mechanical thrombolysis and/or withdrawal of blood samples and for capture of thrombus or emboli.

The embodiments disclosed herein further benefit from a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Another way to view this aspect is that the structure of the filter includes a greater open surface area exposed to the flow of embolic material into the filter at its proximal end, while the distal end has smaller open surface area exposed to the flow of embolic material to capture the embolic material in the distal end of the filter member. More specifically, regardless of whether the embodiments disclosed herein is delivered by a jugular approach or a femoral approach, the filter geometry is such that the larger interstitial openings of the filter are positioned inferiorly along a longitudinal axis of the filter. The embodiments disclosed herein also benefit from combining the functions of an inferior vena cava (IVC) filter and a multilumen central venous catheter. The embodiments disclosed herein may be placed in the inferior vena cava via the femoral vein for the prevention of PE, as well as access to the central venous system.

EXAMPLES

A study compared the ease of in vitro placement, retrieval, deployment, and clot-trapping effectiveness a Vena Cava Filter Catheter (VCFC) utilizing the embodiments disclosed herein compared to other retrievable IVC filters. (Angel L, Guerra R, Atkinson E, et al. *In Vitro Placement and Effectiveness of the Angel™ Vena Cava Filter Catheter*), incorporated by reference herein.

The study was conducted in a vena cava simulator with tubing diameters of 16 mm, 19 mm, 25 mm and 30 mm. Human blood has a mean density of 1.055 g/mL and a mean viscosity of 0.035 St at a mean temperature of 37 C. Therefore, the vena cava simulator mimicked physiological conditions by using a blood analog aqueous solution, composed of a 52% glycerin by weight with a density of 1.12 g/ML and a viscosity of 0.032St that was circulated at $37 \pm 2°$ C.

The filter was expanded as the outer sheath was pulled back and secured in position. The filter was retrieved by reversing the process and collapsing the filter as the multilumen catheter was pulled back into the outer sheath. The filter was tested with 150 cylindrical clots that simulated emboli of four different sizes: 3×5 mm, 3×10 mm, 5×10 mm and 5×20 mm. The clot-trapping effectiveness of the VCFC was compared to other retrievable IVC filters including the Cook Gunther Tulip, Bard Recovery, and Bard G2.

The VCFC utilizing the embodiments disclosed herein was successfully deployed 24 times at various vena cava diameters. All the tested filters were deployed in the required area with full apposition against the wall of the simulated vena cava at all times. No migration was observed post deployment or during the clot capture efficiency testing. Filter efficiency increased proportionally to the cylindrical clot size and inversely to the test tube inner diameter. The clot capturing rate of the VCFC utilizing the embodiments disclosed herein was similar to that of the Tulip, Recovery, and G2 filters at an IVC diameter of 16 mm and 19 mm, but was superior in capturing small clots at a diameter of 25 mm ($p<0.001$). This initial evaluation of the effectiveness of the VCFC utilizing the embodiments disclosed herein shows that it is as effective as predicate filters at various vena cava diameters. The VCFC utilizing the embodiments disclosed herein addresses the important limitations of predicate vena cava filters. Specifically, the VCFC utilizing the embodiments disclosed herein allows for bedside insertion and retrieval for critically ill patients by combining a multilumen central venous catheter and a truly retrievable vena cava filter. Further details on the study of the ease of in vitro placement, retrieval, deployment, and clot-trapping effectiveness the Vena Cava Filter Catheter (VCFC) utilizing the embodiments disclosed herein may be found in Angel L, Guerra R, Atkinson E, et al. *In Vitro Placement and Effectiveness of the Angel™ Vena Cava Filter Catheter.*

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the attachment configuration described herein and to teach the best mode of carrying out the same.

What we claim is:

1. An attachment configuration disposed at a proximal end of a filter member comprising:
   a. a catheter body coaxially disposed through the proximal end of the filter member;
   b. a plurality of cutouts disposed coaxially around the proximal end of the filter member; and
   c. a thin tube coaxially disposed around the plurality of cutouts, wherein the thin tube engages the at least a portion of the catheter body and the thin tube fixedly attaches the proximal end of the filter member through the plurality of cutouts;
   wherein the material of the thin tube and the material of the catheter body is the same as to be fused together through the plurality of cutouts;
   wherein the plurality of cutouts include a width W extending generally along the longitudinal axis of the proximal end and a height H extending generally along the axial axis of the proximal end, wherein the width W of the cutouts is greater than the height H of the plurality of cutouts;
   wherein the plurality of cutouts are longitudinally disposed throughout the proximal end of the filter member to provide at least two longitudinal rows of cutouts
   wherein the at least two longitudinal rows of cutouts is a first row of longitudinal cutouts and a second row of longitudinal cutouts;
      the first longitudinal row of cutouts is a repeating pattern of semi-circular shape cutouts, whereby the semicircular shape cutouts include a first leg and a second encircling the semi-circular cutout;
      the second longitudinal rows of cutout includes a repeating pattern of diamond shaped cutouts, whereby the diamond shaped cutouts include a strut-like enclosure with a top half and a bottom half enclosing the diamond shaped cutouts; and
      the top half and the bottom half of the diamond-shaped cutouts are fixedly attached to the first legs of the semi-circular cutouts.

2. The attachment configuration of claim 1, wherein each longitudinal row of cutouts include at least two cutouts along the longitudinal axis.

3. The attachment configuration of claim 1, wherein the plurality of cutouts are axially disposed through at least portion of the proximal end of the filter member to provide at least two axial columns of cutouts.

4. The attachment configuration of claim 3, wherein the thin tube is coaxially disposed over a first axial column of cutouts and the second axial column of cutouts.

5. The attachment configuration of claim 1, wherein a first end and a second end generally cover at least a portion of the semi-circular cutouts, and the first end and the second end of adjacent diamond-shaped cutouts include a space therebetween.

6. The attachment configuration of claim 5, wherein the distal end of the thin tube is positioned at the space therebetween the first end and the second end of the diamond shaped cutouts.

7. The attachment configuration of claim 5, wherein the attachment configuration is radially expandable.

8. The attachment configuration of claim 1, wherein elliptical shaped cutouts engage a detent projection on the catheter body as to prevent longitudinal movement of the proximal end upon attachment of the thin tube.

9. The attachment configuration of claim 1, wherein the proximal end of the filter member includes a thickness Tp and the plurality of cutouts traverse the entire thickness Tp of the proximal end of the filter member.

10. The attachment configuration of claim 1, wherein the thin tube includes a thickness Tt and the thickness Tt of the thin tube is less than the thickness Tp of the proximal end of the filter member, such that the thin tube traverses the thickness Tp of the proximal end of the filter member to engage the catheter body.

11. The attachment configuration of claim 1, wherein each cutout in the longitudinal row of cutouts is touching adjacent cutouts along the width W of the cutouts.

12. The attachment configuration of claim 1, wherein each adjacent cutouts in each longitudinal row of cutouts includes a space between adjacent ends of the cutouts along the width of the cutouts.

13. The attachment configuration of claim 1, further comprising a placement sensor coupled to the proximal end of the attachment configuration.

14. The attachment configuration of claim 1, wherein the material of the thin tube is selected from the group consisting essentially of: polytetrafluoroethylene (PTFE), ethylene tetrafluoroethylene (ETFE), fluorinated ethylene propylene (FEP), polyoxymethylene, polybutylene terephthalate (PBT), polyether block ester, polyurethane, polypropylene (PP), polyvinylchloride (PVC), polyether-ester, polyester, polyamide, elastomeric polyamides, block polyamide/ethers, polyether block amide (PEBA), silicones, polyethylene (PE), Marlex high-density polyethylene, Marlex low-density polyethylene, linear low density polyethylene, polyethylene terephthalate (PET), polyetheretherketone (PEEK), polyimide (PI), polyetherimide (PEI), polyphenylene sulfide (PPS), polyphenylene oxide (PPO), polysulfone, nylon, nylon-12, perfluoro(propyl vinyl ether) (PFA), ethylene vinyl alcohol, polyolefin, polystyrene, epoxy, polyvinylidene chloride (PVdC), polycarbonates, ionomers, and biocompatible polymers.

15. The attachment configuration of claim 1, wherein the catheter body includes an outer diameter size between about 1.3 mm and 2.4 mm.

16. The attachment configuration of claim 1, wherein the thin tube includes a diameter Dt, the proximal end of the filter member includes a diameter Dp, and the catheter body includes a diameter Dm; wherein the diameter Dt of the thin tube is greater than the diameter Dp of the proximal end of the filter member, and the diameter Dp of the proximal end of the filter member is greater than the diameter Dm of the catheter body.

17. The attachment configuration of claim 1, wherein the thin tube includes a diameter Dt, the proximal end of the filter member includes a diameter Dp, and the catheter body includes a diameter Dm; wherein the diameters Dt, Dp, and Dm are substantially the same.

* * * * *